(12) United States Patent
Arsenault et al.

(10) Patent No.: US 11,168,100 B2
(45) Date of Patent: Nov. 9, 2021

(54) INITIATOR SYSTEM FOR CATIONIC POLYMERIZATION OF OLEFINS

(71) Applicants: ARLANXEO CANADA INC., Sarnia (CA); THE UNIVERSITY OF BRITISH COLUMBIA, Vancouver (CA)

(72) Inventors: Gilles Arsenault, London (CA); Hazin Khatera, Vancouver (CA); Derek Gates, Vancouver (CA)

(73) Assignees: ARLANXEO SINGAPORE PTE. LTD., Singapore (SG); THE UNIVERSITY OF BRITISH COLUMBIA, Vancouver (CA)

( * ) Notice: Subject to any disclaimer, the term of this patent is extended or adjusted under 35 U.S.C. 154(b) by 0 days.

(21) Appl. No.: 16/771,375

(22) PCT Filed: Dec. 14, 2017

(86) PCT No.: PCT/CA2017/051515
§ 371 (c)(1),
(2) Date: Jun. 10, 2020

(87) PCT Pub. No.: WO2019/113674
PCT Pub. Date: Jun. 20, 2019

(65) Prior Publication Data
US 2021/0171550 A1 Jun. 10, 2021

(51) Int. Cl.
*C07F 9/00* (2006.01)
*C08F 4/20* (2006.01)
(Continued)

(52) U.S. Cl.
CPC ............. *C07F 9/005* (2013.01); *C08F 4/20* (2013.01); *C08F 10/10* (2013.01); *C08F 16/18* (2013.01);
(Continued)

(58) Field of Classification Search
CPC ................................ C07F 9/005; C08F 4/20
See application file for complete search history.

(56) References Cited

U.S. PATENT DOCUMENTS 3,361,778 A  1/1968  Pederson
3,919,180 A  11/1975  Furukawa et al.
(Continued)

FOREIGN PATENT DOCUMENTS

CA  203168 A1  8/1991
CA  2235905 A1  10/1998
(Continued)

OTHER PUBLICATIONS

Barthel J, Buestrich R, Carl E, Gores HJ. J.; A New Class of Electrochemically and Thermally Stable Lithium Salts for Lithium Battery Electrolytes: III. Synthesis and Properties of Some Lithium Organoborates; Electrochem. Soc. vol. 143, Nov. 1996, pp. 3572-3575.
(Continued)

*Primary Examiner* — Catherine S Branch
(74) *Attorney, Agent, or Firm* — The Dobrusin Law Firm, P.C.

(57) ABSTRACT

A Brønsted-Lowry acid initiator system for cationic polymerization of an ethylenically unsaturated monomer involves
(Continued)

an initiator having a structure of Formula (I) in an anhydrous polymerization medium:

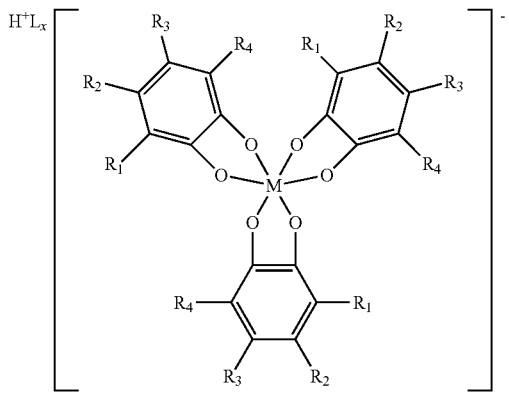

(I)

where: M is tantalum (Ta), vanadium (V) or niobium (Nb); $R_1$, $R_2$, $R_3$ and $R_4$ are the same or different and are independently H, F, Cl, Br, I, alkyl or aryl, or two or more of $R_2$, $R_3$, $R_4$ and $R_5$ on a same benzene ring are taken together to form a bicyclic, tricyclic or tetracyclic moiety with the benzene ring, with the proviso that all of $R_1$, $R_2$, $R_3$ and $R_4$ on the same benzene ring are not H; L is absent or a molecule that coordinates to $H^+$; and, x is 0 when L is absent, or x is 0.5 or more when L is present.

19 Claims, 1 Drawing Sheet

(51) Int. Cl.
| | |
|---|---|
| C08F 10/10 | (2006.01) |
| C08F 16/18 | (2006.01) |
| C08F 112/12 | (2006.01) |
| C08F 116/18 | (2006.01) |
| C08F 210/12 | (2006.01) |

(52) U.S. Cl.
CPC .......... *C08F 112/12* (2013.01); *C08F 116/18* (2013.01); *C08F 210/12* (2013.01); *C08F 2500/03* (2013.01)

(56) References Cited

U.S. PATENT DOCUMENTS

| | | |
|---|---|---|
| 2010/0273964 A1 | 10/2010 | Lewis |
| 2012/0208971 A1 | 8/2012 | Konig et al. |

FOREIGN PATENT DOCUMENTS

| | | |
|---|---|---|
| DE | 19704482 A1 | 8/1998 |
| EP | 3336111 A1 | 6/2018 |
| WO | 2018107295 A1 | 6/2018 |

OTHER PUBLICATIONS

European Search Report and Written Opinion for EP 16204669 dated May 3, 2017.
International Search Report and Written Opinion for PCT/CA2017/051517 dated Feb. 6, 2018.
Toda et al., "Synthesis, Structure, and 1-Hexene Polymerization Catalytic Ability of Group 5 Metal Complexes ncorporating an [OSSO]-Type Ligand" Jul. 8, 2013, ASC Catalysis 3:1764-1767.
Mashima et al., "Polymerization of Ethylene Catalyzed by the System Ta (n5-C5Me5)(n4-diene)CH3)2/MAO: An isoelectronic Analogue for a Group 4 Metallocene Catalyst" Nov. 1, 1993, J. Am. Chem. Soc. 115 (23):10990-10991.
Mashima et al., "Living Polymerization of Ethylene Catalyzed by Diene Complexes of Niobium and Tantalum, M(n5-C5Me5)(n4-diene)X2 and M(n5-C5-Me5)(n4-diene)2(M=Nb and Ta), in the Presence of Methylaluminoxane", Jun. 1, 1995, Organometallics 14(6):2633-2640.
Ei-Khafaji et al., "Tetraphenolate Niobium and Tantalum Complexes for the Ring Opening Polymerization of e-caprolactone" Feb. 18, 2015, Dalton Trans. 44(27):12349-12356.
Sun et al. "Al-, Nb-, and Ta-Based Perfluoroaryloxide Anions and Cocatalysts for Metallocene-Mediated Ziegler-Natta Olefin Polymerization" May 1, 2000, Organometallics 19(9):1625-1627 (6 pp. total).
McManus et al., "The Refractive Index Increment for Poly-a-Methylstyrene at 633 nm in Tetrahydrofuran", J_ Appl. Dolym. Sci., Dec. 7, 1998, vol. 70(6), pp. 1253-1254.
Jackson et al., "Size Exclusion Chromatography with Multiple Detectors: Solution Properties of Linear Chains of Varying Flexibility in Tetrahydrofuran", J. Appl. Polym. Sci., Aug. 1, 1996, vol. 61(5), pp. 865-874.
International Search Report and Written Opinion, PCT Application No. PCT/CA2017/051515 dated Aug. 15, 2018.
International Preliminary Report on Patentability, PCT Application No. PCT/CA2017/051515 dated Jun. 16, 2020.
Lübbecke H., Boldt P., Quinonwa-VII[1], Halogen and Oxidative Halogenation of Phenols Halides/Hydrogen Peroxide; Tetrahedon 1078, vol. 34, pp. 1577-1579.
Aviva Levina, et al., Vanadium Speciation by XANES Spectroscopy: A Three-Dimensional Approach, Chemistry—A European Journal, Sep. 15, 2014 Wiley—V C H Verlag GmbH & Co. KGaA, DE, vol. 20, Nr: 38, pp. 12056-12060.
Cindy-Xing Yin, et al., Vanadium-Based, Extended Catalytic Lifetime Catechol Dioxygenases: Evidence for a Common Catalyst, Journal of the American Chemical Society, Jun. 1, 2005 American Chemical Society, US, vol. 127, Nr: 25, pp. 9003-9013.
Klaus Andrea, Cyclic Niobium (V) and Tantalum (V) Acid Esters-Cyclische Niob(V)-Und Tantal(V)S~Ureester, Journal of the Less Common Metals, Jan. 1, 1969, vol. 17, Nr: 3, pp. 297-303.
Calderazzo F, Pampaloni G, Reactions of Hexacarbonyl Derivatives of Group 5 Metals (V, Nb, Ta) With 9,10-Phenanthrenequinone, Journal of Organometallic Chemistry, Aug. 18, 1987 Elsevier, Amsterdam, NL, vol. 330, Nr: 1-2, pp. 47-59.
Stephen R Cooper, et al., Synthetic, structural, and physical studies of bis(triethylammonium) tris(catecholato)vanadate(IV), potassium bis(catecholato)oxovanadate(IV), and potassium tris(catecholato)vanadate (III), Journal of the American Chemical Society, Sep. 1, 1982 American Chemical Society, US, vol. 104, Nr: 19, pp. 5092-5102.

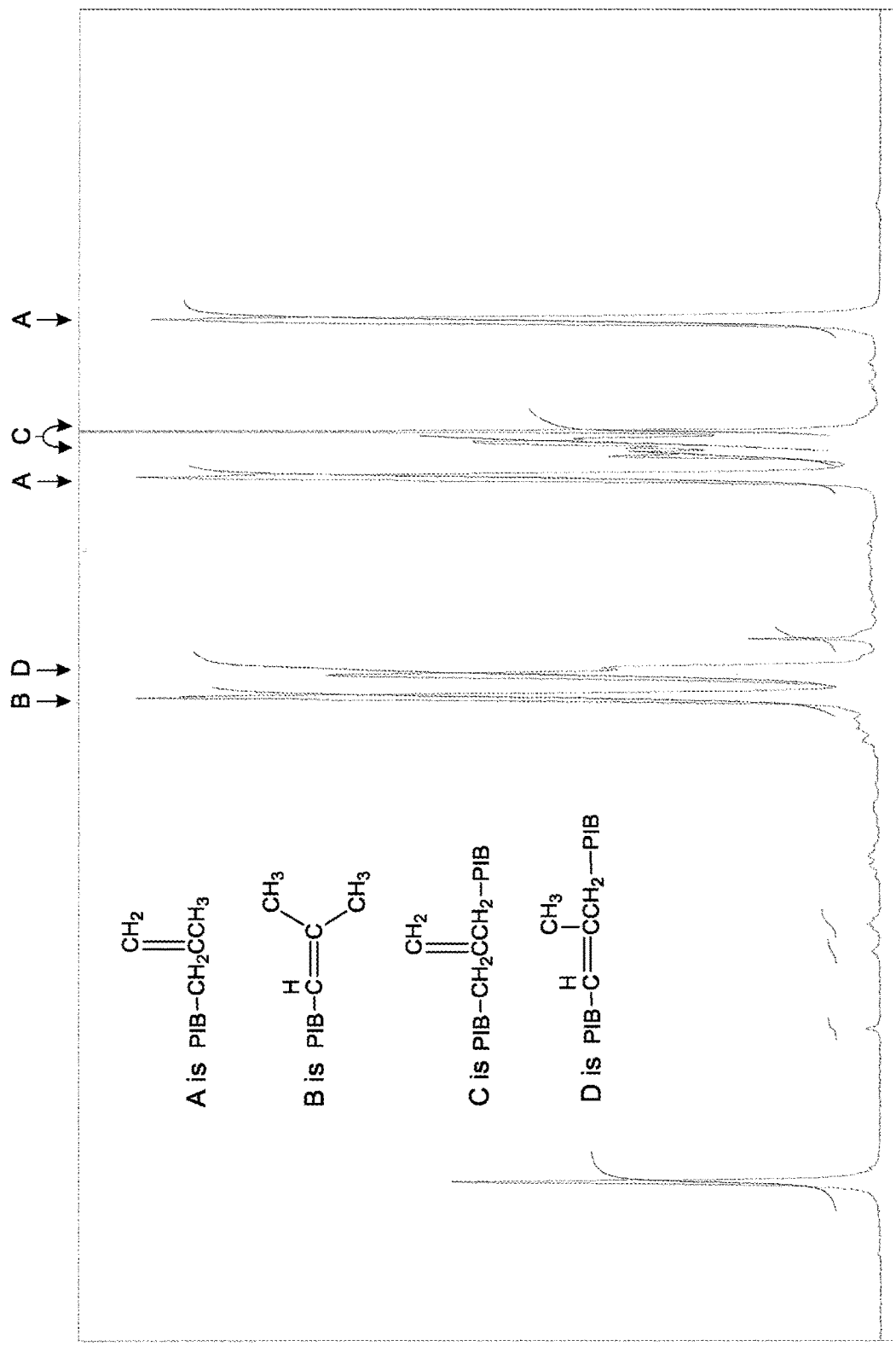

INITIATOR SYSTEM FOR CATIONIC POLYMERIZATION OF OLEFINS

FIELD

This application relates to a process for producing a polymer from one or more ethylenically unsaturated monomers. The application further relates to an initiator system for the process, and to compounds in the initiator system.

BACKGROUND

Various types of initiator systems for cationic polymerization of ethylenically unsaturated monomers are known in the art, including systems based on protonic or Brønsted-Lowry acids, Lewis acids (e.g. Friedel-Crafts catalysts), carbenium ion salts and ionizing radiation. Common protonic acids include phosphoric, sulfuric, fluoro-, and triflic acids, which tend to produce only low molecular weight polymers.

Lewis acids are the most common compounds used for initiation of cationic polymerization, and include, for example, $SnCl_4$, $AlCl_3$, $BF_3$ and $TiCl_4$. Although Lewis acids alone may be able to induce polymerization, the reaction occurs much faster with a co-initiator that acts as a suitable cation source (e.g. water, alcohols, HCl). However, such cationic polymerization reactions generally require very low temperature (about −100° C. to about −90° C.) to produce polymers of suitable molecular weight. Further, polymerization processes performed at such low temperatures are energy intensive; therefore, a process that can produce polymers with similar molecular weights at higher temperatures would significantly reduce the energy consumption and manufacturing cost of the process.

Recently, an initiator system for cationic polymerization has been developed based on a pentavalent phosphorus (V) complex with a dihydroxy compound (United States Patent Publication US 2012/0208971 published Aug. 16, 2012). However, this initiator system produces low molecular weight products at higher temperatures, requiring lower temperatures to produce polymers of desirably high molecular weight. For example, the polymerization of α-methyl styrene at −50° C. produces poly(α-methylstyrene) having $M_n$ of less than about 7000 g/mol, Further, in order to produce polystyrene having $M_n$ of greater than 100,000 g/mol, the polymerization must be done at temperatures lower than −80° C. The phosphorus complex can also be difficult to handle due to lack of stability.

There remains a need for initiator systems for cationic polymerization, which can produce suitably high molecular weight polymer at higher temperatures.

SUMMARY

A strong Brønsted-Lowry acid based on complexes of tantalum (V) ions or other isoelectronic metal ions (e.g. vanadium (V) or niobium (V) ions) provides an efficient initiator system for cationic polymerization of ethylenically unsaturated monomers at higher temperatures. High molecular weight polymers may be formed with the use of the present initiator system at higher temperatures.

In one aspect, there is provided a process for producing a polymer, the process comprising polymerizing one or more ethylenically unsaturated monomers under anhydrous conditions in presence of a Brønsted-Lowry acid polymerization initiator, the Brønsted-Lowry acid polymerization initiator having a structure of Formula (I):

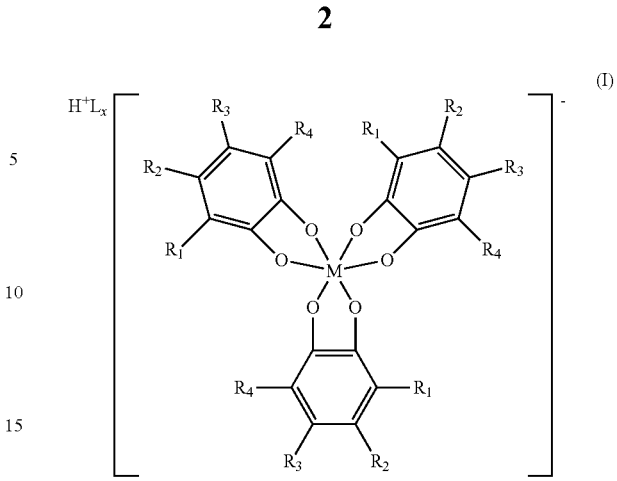

where:
M is tantalum (Ta), vanadium (V) or niobium (Nb);
$R_1$, $R_2$, $R_3$ and $R_4$ are the same or different and are independently H, F, Cl, Br, I, alkyl or aryl, or two or more of $R_2$, $R_3$, $R_4$ and $R_5$ on a same benzene ring are taken together to form a bicyclic, tricyclic or tetracyclic moiety with the benzene ring, with the proviso that all of $R_1$, $R_2$, $R_3$ and $R_4$ on the same benzene ring are not H;
L is absent or a molecule that coordinates to $H^+$; and,
x is 0 when L is absent, or x is 0.5 or more when L is present.

In another aspect, there is provided a Brønsted-Lowry acid initiator system for cationic polymerization of an ethylenically unsaturated monomer, the Brønsted-Lowry acid initiator system comprising an initiator having a structure of Formula (I) as defined above in an anhydrous polymerization medium.

In another aspect, there is provided a compound of Formula (I), where M, $R_1$, $R_2$, $R_3$, $R_4$, L and x are as defined above.

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, preferred embodiments will now be described in detail by way of example, with reference to the accompanying drawings, in which:

FIG. 1 is a $^1H$ NMR spectrum of polyisobutylene (PIB) produced using Initiator (Ill).

DETAILED DESCRIPTION

The strong Brønsted-Lowry acid comprises a metal complex of organic ligands as described above for Formula (I).
M is preferably tantalum.
When two or more of $R_1$, $R_2$, $R_3$ and $R_4$ on a same benzene ring are taken together to form a bicyclic, tricyclic or tetracyclic moiety with the benzene ring, the moiety is preferably a fused ring system, for example a naphthyl moiety or an anthracyl moiety. $R_1$, $R_2$, $R_3$ and $R_4$ are preferably independently H, F, Cl, Br, I, alkyl or aryl, with the proviso that all of $R_1$, $R_2$, $R_3$ and $R_4$ on the same benzene ring are not H. More preferably, $R_1$, $R_2$, $R_3$ and $R_4$ are independently H, F, Cl or Br, with the proviso that all of $R_1$, $R_2$, $R_3$ and $R_4$ on the same benzene ring are not H. When $R_1$, $R_2$, $R_3$ and $R_4$ on the same benzene ring are both hydrogen and halogen (e.g. F, Cl, Br), the benzene ring may be mono-, di- or tri-halogenated, preferably di- or tri-halogenated. Preferably, $R_1$, $R_2$, $R_3$ and $R_4$ are all independently F, Cl or Br. More preferably, $R_1$, $R_2$, $R_3$ and $R_4$ are independently F or Cl. Even more preferably, $R_1$, $R_2$, $R_3$ and $R_4$ are the same and are F or Cl, which provides for tetra-fluorinated or tetra-chlorinated benzene rings.

Alkyl is preferably $C_{1-6}$alkyl, more preferably $C_{1-4}$ alkyl (e.g. methyl, ethyl, n-propyl, i-propyl, n-butyl, s-butyl, t-butyl), even more preferably methyl. Alkyl may be unsubstituted or substituted by one or more substituents. Substituents may be, for example, F, Cl, Br or aryl. Aryl is preferably $C_{1-18}$ aryl, more preferably $C_{1-10}$ aryl, even more preferably $C_{1-6}$ aryl, for example phenyl. Aryl may be unsubstituted or substituted by one or more substituents. Substituents may be, for example, F, Cl, Br or alkyl, where alkyl is as defined above.

In one embodiment, M is Ta; $R_1$, $R_2$, $R_3$ and $R_4$ are F or Cl; L is $Et_2O$ and x is 2. In another embodiment, M is Ta; $R_1$, $R_2$, $R_3$ and $R_4$ are F or Cl; L is $Et_2O$ and x is 2.

The Brønsted-Lowry acid polymerization initiator is particularly useful for initiating the polymerization or copolymerization of ethylenically unsaturated monomers. Ethylenically unsaturated monomers are compounds having at least one olefin bond therein. The monomers preferably comprise from 2 to 20 carbon atoms. Some examples of ethylenically unsaturated monomers include alkyl vinyl compounds (e.g. alkyl vinyl ethers and the like), aryl vinyl compounds (e.g. styrene, α-methylstyrene, p-methylstyrene, p-methoxystyrene, 1-vinylnaphthalene, 2-vinylnaphthalene, 4-vinyltoluene and the like), isobutylene and isoprene. Of particular note are n-butyl vinyl ether, styrene, α-methylstyrene, isobutylene and isoprene.

Polymers formed from the polymerization of the monomers may be homopolymers, copolymers, terpolymers or other forms of polymers. The polymers may be linear, branched or star branched. Mixtures of two or more monomers may be polymerized into copolymers or terpolymers. Some examples of polymers include polystyrene, poly(α-methylstyrene), poly(N-vinylcarbazole), polyterpenes, polyisoprenes, polyisobutylenes and the like. Of particular note are copolymers of isobutylene and isoprene (e.g. butyl rubber), polyisobutylene, polyisoprene, polystyrenes (e.g. polystyrene and poly(α-methylstyrene) and poly(n-butyl vinyl ether).

Polymers produced in the polymerization of ethylenically unsaturated monomers may have number average molecular weights (Mn) of at least about 2,000 g/mol, or at least about 5,000 g/mol, or at least about 10,000 g/mol, or at least about 20,000 g/mol, or at least about 30,000 g/mol, or at least about 50,000 g/mol, or at least about 100,000 g/mol, depending on the monomer or momomers undergoing polymerization, the relative amounts of monomer and initiator, the temperature at which the polymerization is conducted and other process conditions. The polymer may have number average molecular weights (Mn) up to about 1,000,000 g/mol, or up to about 500,000 g/mol, or up to about 250,000 g/mol.

The initiator is a cationic initiator because the initiator is a Brønsted-Lowry acid, thereby further comprising a hydrogen ion ($H^+$) as counterion to an anionic metal complex. The hydrogen ion may be associated as a "naked" ion with the metal complex (i.e. x=0). To stabilize the hydrogen ion, the initiator may further comprise a stabilizing molecule (L) for the hydrogen ion. The stabilizing molecule is a molecule that is able to stabilize the hydrogen ion without making the hydrogen ion unavailable for catalyzing the polymerization. The value of x may be an integer or a fractional number depending on whether $H^+$ ions associated with neighboring complexes in a bulk material of the polymerization initiator share a molecule, L. When a molecule L is shared between neighboring $H^+$ ions, the value of x may be fractional. The value of x is preferably 0.5, 1, 1.5, 2, 2.5 or 3. In one embodiment, there are two stabilizing molecules for each $H^+$ ion (i.e. x=2). The stabilizing molecule may be a molecule that can form hydrogen bonds with the hydrogen ion. The stabilizing molecule may therefore contain one or more atoms that have lone pairs of electrons, for example O or N atoms. Sterically-hindered stabilizing molecules having one or more lone pairs of electrons are particularly useful as they sufficiently stabilize the hydrogen ion while permitting the hydrogen ion to initiate carbocationic polymerization. Some examples of stabilizing molecules include ethers and the like. Aprotic stabilizing molecules are preferred. Alkyl and cycloalkyl ethers are particularly preferred. Some examples of suitable stabilizing molecules are tetrahydrofuran, tetrahydropyran, dioxane, dimethyl ether, diethyl ether, bis(2-chloroethyl) ether, dipropyl ether, diisopropyl ether, methyl ethyl ether, methyl n-propyl ether, methyl isopropyl ether, bis(2-chloroisopropyl) ether, methyl tert-butyl ether, ethyl tert-butyl ether, diisobutyl ether, dihexyl ether, 2,5-dimethyltetrahydrofuran, 2-chloroethyl ether, 2-methyltetrahydrofuran, cyclopentyl methyl ether, diethylene glycol dimethyl ether (diglyme), tetraethylene glycol dimethyl ether, diphenyl ether, 2,6-di-tert-butyl pyridine and the like. In one embodiment, the stabilizing molecule is diethyl ether. Where the stabilizing molecule is a solvent, the stabilizing molecule may form a solvate with the hydrogen ion.

The compound of Formula (I) may be synthesized by contacting a metal ion precursor compound in a reaction mixture with an organic α-,β-dihydroxy ligand compound of Formula (II):

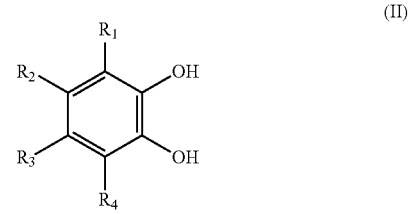

(II)

where $R_1$, $R_2$, $R_3$ and $R_4$ are as defined above. Mixtures of different organic ligand compounds may be used.

The metal ion precursor compound and organic ligand compounds may be present in the reaction mixture in amounts to provide a molar ratio that results in the metal complex having sufficient ligands to provide a negative charge to the metal complex. To provide metal complexes of the Formula (I), about 3 molar equivalents of the organic α-,β-dihydroxy ligand compound of Formula (II) is suitable to result in the metal complex having three bidentate ligands.

The metal ion precursor compound may be a compound of a metal ion with leaving groups as ligands. Suitable leaving groups include, for example, halogen (Cl, Br), CO, CN and the like. The metal ion precursor compound and organic ligand compounds are preferably dry and high purity. Contacting the metal ion precursor compound with the organic ligand compounds may be performed in the presence or absence of a solvent, preferably in the presence of a solvent. The solvent may comprise an aprotic organic solvent, preferably a non-coordinating solvent. Some examples of suitable solvents include alkyl halides (e.g. dichloromethane), aromatic hydrocarbons (e.g. toluene) and acetonitrile. A stabilizing molecule for hydrogen ions may be included in the reaction mixture, preferably after the metal complex is formed, to solvate the hydrogen ion. The reaction is preferably conducted under anhydrous conditions. The reaction may be conducted at elevated temperature, for example by refluxing the solvent. The reaction may be conducted for an amount of time sufficient to maximize the yield of the initiator, for example for a time up to about 3 hours. The reaction is preferably conducted by slowly adding the ligand compound to a reaction mixture containing the metal ion precursor compound, although other addition schemes may be used. The initiator may be recovered from the reaction mixture by standard techniques, for example filtration, washing, recrystallization and drying.

The initiator is preferably used in amount to provide a monomer to initiator mole ratio ([M]:[I]) of at least about 20:1. A higher [M]:[I] may be preferred in some embodiments to produce high yields of high molecular weight polymer. In some embodiments, the [M]:[I] may be at least about 100:1. In some embodiments, the [M]:[I] may be in a range of about 100:1 to about 1000:1, or about 200:1 to about 800:1, or about 300:1 to about 500:1.

The polymerization is generally conducted in a polymerization medium. The polymerization medium may be provided, for example, by a solvent or diluent. Solvents or diluents for the polymerization may include, for example a halogenated organic liquid, a non-halogenated organic liquid or mixtures thereof. Halogenated organic liquids include, for example, chlorinated or fluorinated organic compounds. Chlorinated organic compounds include, for example C1-C4 alkyl chlorides (e.g. dichloromethane (DCM) and methyl chloride (MeCl)). DCM is generally useful as a solvent for solution polymerization, while MeCl is generally useful as a diluent for slurry polymerization. Fluorinated organic compounds include, for example, hydrofluorocarbons (HFC) such as 1,1,1,2-tetrafluoroethane and the like, and hydrofluorinated olefins (HFO) such as 2,3,3,3-tetrafluoro-1-propene and the like. Fluorinated organic compounds are generally useful as diluents for slurry polymerization. Non-halogenated organic liquids include, for example, aliphatic hydrocarbons (e.g. cyclohexane, cyclopentane, 2,2-dimethylbutane, 2,3-dimethylbutane, 2-methylpentane, 3-methylpentane, n-hexane, methylcyclopentane and 2,2-dimethylpentane). Halogenated organic solvents, in particular C1-C4 alkyl chlorides are preferred. Dichloromethane ($CH_2Cl_2$) or methyl chloride (MeCl) are particularly preferred.

The solvent or diluent is preferably present in the polymerization medium in an amount of about 10-80 vol %, based on volume of the polymerization medium. In preferred embodiments, the medium may comprise a diluent in an amount of about 55-80 vol %, or a solvent in an amount of about 10-50 vol %.

The polymerization is conducted under anhydrous conditions. Preferably, water is present in an amount less than about 1 ppm, more preferably less than about 0.5 ppm, yet more preferably less than about 0.1 ppm. It is preferable to eliminate water from the polymerization medium altogether. Reducing or eliminating moisture in the polymerization medium helps to produce polymers having higher molecular weights at higher yields.

It is an advantage of the present initiator system that the polymerization may be conducted at a higher temperature than with other Brønsted-Lowry acid or Lewis acid initiator systems, while being able to produce suitably high molecular weight polymers at good yield. The temperature at which the polymerization is conducted may be −90° C. or higher, or −85° C. or higher, or −80° C. or higher, or −70° C. or higher, or −60° C. or higher, or −50° C., or −40° C. or higher. The temperature may be as high as 30° C. or lower, or 20° C. or lower, or 10° C. or lower, or 0° C. or lower, or −10° C. or lower, or −15° C. or lower, or −20° C. or lower, or −25° C. or lower, −30° C. or lower, or −35° C. or lower.

EXAMPLES

General Materials and Procedures:

All experiments were performed using standard Schlenk or glove box techniques under nitrogen atmosphere.

Dichloromethane ($CH_2Cl_2$) and diethyl ether ($Et_2O$) were deoxygenated with nitrogen and dried by passing through a column containing activated alumina. Tetrahydrofuran (THF) (Fisher Scientific) was dried and distilled over benzophenone ketyl prior to use. $CH_2Cl_2$ (Sigma Aldrich), $Et_2O$ (Fisher Scientific), styrene (Sigma Aldrich) and n-butyl vinyl ether (Sigma Aldrich) were dried over calcium hydride, distilled and freeze-pump-thaw (x3) degassed prior to use. $CH_2Cl_2$, $Et_2O$ and methyl tert-butyl ether were stored over molecular sieves prior to use.

Tantalum pentachloride (Aldrich) and niobium pentachloride (Aldrich) were used without further purification. Tetrachlorocatechol was prepared following the procedure described in Lübbecke H., Boldt P. *Tetrahedron* 1978, 34, 1577-1579, the contents of which is herein incorporated by reference, and then azeotropically distilled and recrystallized from hot toluene prior to use. Tetrafluorocatechol was prepared following a literature procedure described in Barthel J, Buestrich R, Carl E, Gores H J. *J. Electrochem. Soc.* 1996, 143, 3572-3575, the contents of which is herein incorporated by reference. Hexafluoro-2,3-bis(trifluoromethyl)-2,3-butanediol (Matrix Scientific) and 3-fluorocatechol (Sigma Aldrich) were used without further purification.

$^1H$ and $^{13}C\{^1H\}$ NMR spectra were recorded on Bruker Avance 300 or 400 MHz spectrometers at room temperature unless noted. $^1H$ NMR and $^{13}C\{^1H\}$ NMR spectra were referenced to deuterated solvents.

Molecular weight of polymers was determined by triple detection gel permeation chromatography (GPC-LLS) utilizing an Agilent 1260 Series standard auto sampler, an Agilent 1260 series isocratic pump, Phenomenex Phenogel™ 5 μm narrowbore columns (4.6×300 mm) $10^4$ Å (5000-500,000), 500 Å (1,000-15,000), and $10^3$ Å (1,000-75,000), a Wyatt Optilab™ rEx differential refractometer (λ=658 nm, 25° C.), as well as a Wyatt tristar miniDAWN (laser light scattering detector (λ=690 nm)) and a Wyatt ViscoStar viscometer. Samples were dissolved in THF (ca. 2 mg $mL^{-1}$) and a flow rate of 0.5 mL $min^{-1}$ was applied. The differential refractive index (dn/dc) of poly(n-butyl vinyl ether) (dn/dc=0.068 mL $g^{-1}$) in THF was calculated by using Wyatt ASTRA software 6.1. The differential refractive index (dn/dc) of poly(styrene) (dn/dc=0.185 mL $g^{-1}$) and of poly(α-methylstyrene) (dn/dc=0.204 mL $g^{-1}$) has been reported in McManus N T, Penlidis A. *J. Appl. Polym. Sci.* 1998, 70, 1253-1254. The differential refractive index (dn/dc) of poly(isoprene) (dn/dc=0.129 mL $g^{-1}$) (Jackson C, Chen Y J, Mays J W. *J. Appl. Polym. Sci.* 1996, 61, 865) has been reported.

Initiator (III):

Synthesis of H(OEt$_2$)$_2$[Ta(1,2-O$_2$C$_6$Cl$_4$)$_3$] (III)

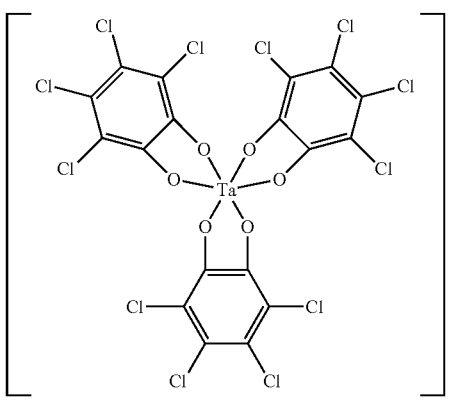

(III)

H(OEt$_2$)$_2$

TaCl$_5$ (0.48 g, 13.4 mmol) was stirred in anhydrous CH$_2$Cl$_2$ (6 mL) and the white suspension was slowly heated to reflux under N$_2$ atmosphere. In another Schlenk flask, tetrachlorocatechol (1.00 g, 40.3 mmol) was prepared in warm anhydrous CH$_2$Cl$_2$ (6 mL) and the bright orange-red solution was added via cannula to the refluxing TaCl$_5$ solution at 90° C. to afford a dark green reaction mixture. After 10 min, a faint green precipitate was obtained. The reaction mixture was refluxed for 100 min and cooled to ambient temperature. Upon addition of Et$_2$O (22 mL), a green clear solution formed. The solution was cooled in an ice bath to afford a green precipitate within 20 min. The solid was collected by filtration, washed with CH$_2$Cl$_2$ (3 mL) and dried in vacuo. Yield=(1.28 g, 11.9 mmol, 89% based on TaCl$_5$).

$^1$H NMR (400 MHz, CD$_2$Cl$_2$, 25° C.): δ=7.54 (br, 1H, H(OEt$_2$)$_2$), 4.00 (br, 8H, CH$_2$CH$_3$), 1.40 ppm (br, 12H, CH$_2$CH$_3$).

$^1$H NMR (400 MHz, CD$_2$Cl$_2$, −85° C.): δ=16.74 (s, 1H, H(OEt$_2$)$_2$), 4.04 (br, 8H, CH$_2$CH$_3$), 1.38 (br, 12H, CH$_2$CH$_3$).

$^{13}$C{$^1$H} NMR (75 MHz, CD$_2$Cl$_2$, 25° C.): δ=140.4 (s, Ar—C), 123.4 (s, Ar—C), 118.9 (s, Ar—C), 67.9 (s, OCH$_2$CH$_3$), 14.2 (s, OCH$_2$CH$_3$) ppm.

Elemental analysis (%) found: C, 27.51; H, 1.74. Calcd. for C$_{26}$H$_{21}$Cl$_{12}$O$_8$Ta.1.35 CH$_2$Cl$_2$: C, 27.78; H, 2.02.

MALDI-TOF MS (355 nm) m/z=918.6 [M]$^−$.

Polymerization of Monomers Using Initiator (III)

Polymerization of monomers with initiator (III) was performed by the following general procedure.

Initiator and monomer are initially stored at −30° C. inside a freezer in a glovebox under a positive atmosphere of dry N$_2$ gas. The initiator (0.010 g, 0.010 mmol) is transferred to a 25 mL Schlenk flask, which is sealed with a rubber septum and then brought outside the glovebox maintaining isolation from the outside atmosphere to be connected to a dry N$_2$ gas line. The initiator in the flask is cooled to −78° C. with an acetone/dry ice bath. Anhydrous, degassed CH$_2$Cl$_2$ (2.0 mL) stored over activated molecular sieves is added via syringe to the initiator under a flow of dry N$_2$ gas and stirred to guarantee a homogenous solution at −78° C. The mixture is kept at −78° C. for 10 minutes, or warmed or cooled to a different desired temperature and held at that temperature for 10 minutes, before addition of the monomer.

Freshly prepared and degassed monomer in an amount to achieve a desired monomer to initiator ratio ([M]:[I]) is collected in a 1 ml single-use plastic syringe inside the glovebox. The monomer is then injected rapidly through the rubber septum on the Schlenk flask into the initiator solution at the desired temperature under a constant flow of dry N$_2$ gas, and the reaction mixture is continuously stirred for 15 minutes while polymerization occurs. After the 15 minutes, the reaction is quenched with 0.2 mL of a solution of NH$_4$OH in MeOH (10 vol %), the Schlenk flask is removed from the cooling bath and all volatiles are removed in vacuo. The crude product is dissolved in 2 mL CH$_2$Cl$_2$ and added one drop at a time via syringe to vigorously stirred MeOH (40 mL) to precipitate an oily residue. The polymer is collected by centrifugation and dried in vacuo. Absolute molecular weight (Mn) is determined using triple-detection GPC.

Effect of Temperature on n-Butyl Vinyl Ether Polymerization

TABLE 1 shows data for the polymerization of n-butyl vinyl ether using initiator (Ill) at different temperatures. The data for each example represents the average of at least three separate polymerization reactions. Mn calc.=40,000 g/mol. TABLE 1 shows that significant yield of poly(n-butyl vinyl ether) having a reasonably high molecular weight (Mn) can be achieved at temperatures well above −90° C.

TABLE 1

| Ex. | T (° C.) | [M]:[I] | Yield (%) | M$_n$ (g/mol) | PDI |
| --- | --- | --- | --- | --- | --- |
| 1 | 19.3 | 400 | 33 | 16,300 | 1.54 |
| 2 | 0 | 400 | 31 | 19,400 | 1.69 |
| 3 | −50 | 400 | 61 | 18,200 | 1.57 |
| 4 | −78 | 400 | 72 | 34,100 | 1.45 |
| 5 | −84 | 400 | 77 | 53,100 | 1.14 |

Effect of Temperature on α-Methyl Styrene Polymerization

TABLE 2 shows data for the polymerization of α-methyl styrene using initiator (Ill) at different temperatures. The data for each example represents the average of at least three separate polymerization reactions. Mn calc.=40,000 g/mol. TABLE 2 shows that good balance of high yield and high molecular weight for poly(α-methylstyrene) can be achieved at temperatures much higher than −90° C.

TABLE 2

| Ex. | T (° C.) | [M]:[I] | Yield (%) | M$_n$ (g/mol) | PDI |
| --- | --- | --- | --- | --- | --- |
| 6 | 19 | 400 | 1 | n.d. | n.d. |
| 7 | 0 | 400 | 38 | 3,500 | 1.67 |
| 8 | −38 | 400 | 75 | 10,100 | 1.86 |
| 9 | −50 | 400 | 65 | 17,000 | 1.59 |
| 10 | −78 | 400 | 53 | 205,000 | 1.28 | n.d. = not determined

Initiator (IV):

Synthesis of H(CH$_3$)$_3$COCH$_3$)$_2$[Ta(1,2-O$_2$C$_6$Cl$_4$)$_3$] (IV)

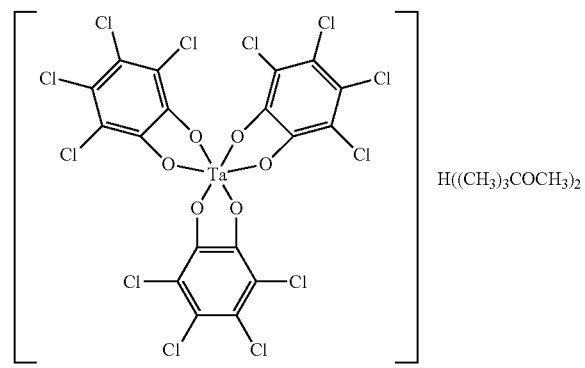

(IV)

The synthesis of initiator (III) described above may be adapted to replace diethyl ether with methyl tert-butyl ether as the coordinating ligand for the proton to afford H(CH$_3$)$_3$COCH$_3$)$_2$[Ta(1,2-O$_2$C$_6$Cl$_4$)$_3$] (IV).

Thus, TaCl$_5$ (0.22 g, 6.2 mmol) was stirred in anhydrous CH$_2$Cl$_2$ (6 mL) and the white suspension was slowly heated to reflux under N$_2$ atmosphere. In another Schlenk flask, tetrachlorocatechol (0.46 g, 18.5 mmol) was prepared in warm anhydrous CH$_2$Cl$_2$ (8 mL) and the bright orange-red solution was added via cannula to the refluxing TaCl$_5$ solution at 90° C. to afford a dark green reaction mixture. After 10 min, a colorless precipitate was obtained. The reaction mixture was refluxed for 85 min and cooled to ambient temperature. Upon addition of methyl tert-butyl ether (16 mL), a green clear solution formed. The solution was cooled in an ice bath to afford a small amount of a light green precipitate within 60 min. The reaction mixture was pumped down to dryness and washed with CH$_2$Cl$_2$ (2 mL) and dried in vacuo. Yield=(0.30 g, 2.7 mmol, 44% based on TaCl$_5$).

$^1$H NMR (400 MHz, CD$_2$Cl$_2$, 25° C.): δ=8.35 (br, 1H, H[(CH$_3$)$_3$COCH$_3$)]$_2$), 3.24 (br, 6H, (CH$_3$)$_3$COCH$_3$)), 1.22 (br, 18H, (CH$_3$)$_3$COCH$_3$)).

$^1$H NMR (400 MHz, CD$_2$Cl$_2$, −85° C.): δ=16.18 (s, 1H, H[(CH$_3$)$_3$COCH$_3$)]$_2$), 3.30 (br, 6H, (CH$_3$)$_3$COCH$_3$)), 1.21 ppm (br, 18H, (CH$_3$)$_3$COCH$_3$)) ppm.

Elemental analysis (%) found: C, 30.39; H, 2.30. Calcd. for C$_{28}$H$_{25}$Cl$_{12}$O$_8$Ta: C, 30.69; H, 2.30. MALDI-TOF MS (355 nm) m/z=918.9 [M]$^-$.

Polymerization of Monomers Using Initiator (IV)

Polymerization of monomers with initiator (IV) was performed by following the general procedure described above for initiator (III). TABLE 3 shows data for the polymerization of n-butyl vinyl ether. TABLE 3 shows that good balance of high yield and high molecular weight for poly(n-butyl vinyl ether) can be achieved at temperatures much higher than −90° C.

TABLE 3

| Ex. | Monomer | T (° C.) | [M]:[I] | Yield (%) | M$_n$ (g/mol) | PDI |
|---|---|---|---|---|---|---|
| 11 | n-butyl vinyl ether | 19.8 | 400 | 37 | 17,300 | 1.55 |
| 12 | n-butyl vinyl ether | 0 | 400 | 66 | 16,600 | 1.62 |
| 13 | n-butyl vinyl ether | −50 | 400 | 71 | 30,200 | 1.87 |
| 14 | n-butyl vinyl ether | −78 | 400 | 76 | 46,900 | 1.29 |

Initiator (V):

Synthesis of H(THF)$_2$[Ta(1,2-O$_2$C$_6$Cl$_4$)$_3$] (V)

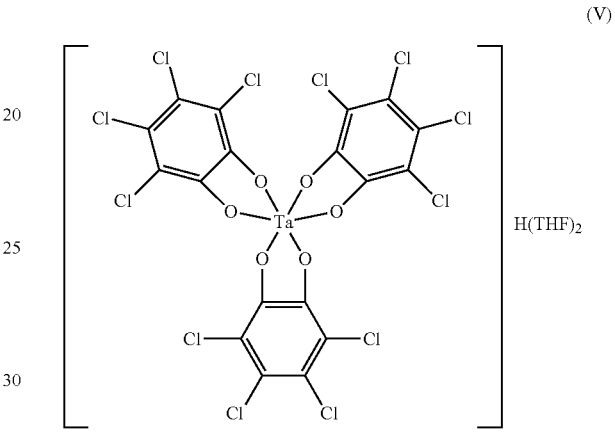

(V)

The synthesis of initiator (III) described above may be adapted to replace diethyl ether with tetrahydrofuran (THF) as the coordinating ligand for the proton to afford H(THF)$_2$[Ta(1,2-O$_2$C$_6$Cl$_4$)$_3$] (V).

Thus, TaCl$_5$ (0.37 g, 10.4 mmol) was stirred in anhydrous CH$_2$Cl$_2$ (6 mL) and the white suspension was slowly heated to reflux under N$_2$ atmosphere. In another Schlenk flask, tetrachlorocatechol (0.77 g, 31.2 mmol) was prepared in warm anhydrous CH$_2$Cl$_2$ (6 mL) and the bright orange-red solution was added via cannula to the refluxing TaCl$_5$ solution at 90° C. to afford a dark green reaction mixture. After 10 min, a colorless precipitate was obtained. The reaction mixture was refluxed for 120 min and cooled to ambient temperature. Upon addition of THF (2 mL), a green clear solution formed. The solution was cooled in an ice bath to afford a small amount of light green precipitate within 30 min. The solid was pumped down to dryness, washed with CH$_2$Cl$_2$ (2 mL) and dried in vacuo. Yield=(0.74 g, 6.9 mmol, 67% based on TaCl$_5$).

$^1$H NMR (400 MHz, CD$_2$Cl$_2$, 25° C.): δ=6.42 (br, 1H, H(THF$_2$), 4.34 (br, 8H, OCH$_2$CH$_2$), 2.08 ppm (br, 8H, OCH$_2$CH$_2$).

$^1$H NMR (400 MHz, CD$_2$Cl$_2$, −85° C.): δ=16.97 (s, 1H, H(THF)$_2$), 3.92 (br, 8H, OCH$_2$CH$_2$), 1.96 ppm (br, 8H, OCH$_2$CH$_2$).

Elemental analysis (%) found: C, 29.26; H, 1.79. Calcd. for C$_{26}$H$_{17}$Cl$_{12}$O$_3$Ta: C, 29.36; H, 1.61.

MALDI-TOF MS (355 nm) m/z=918.5 [M]$^-$.

Polymerization of Monomers Using Initiator (V) Polymerization of monomers with initiator (V) was performed by following the general procedure described above for initiator (Ill). TABLE 4 shows data for the polymerization of n-butyl vinyl ether, styrene and α-methyl styrene using initiator (V). TABLE 4 shows that good balance of high yield and high molecular weight for poly(n-butyl vinyl ether), poly(styrene) and poly(α-methylstyrene) can be achieved at temperatures much higher than −90° C.

TABLE 4

| Ex. | Monomer | T (° C.) | [M]:[I] | Yield (%) | $M_n$ (g/mol) | PDI |
| --- | --- | --- | --- | --- | --- | --- |
| 15 | n-butyl vinyl ether | 19.3 | 400 | 14 | 20,400 | 1.59 |
| 16 | n-butyl vinyl ether | 0 | 400 | 48 | 19,300 | 1.61 |
| 17 | n-butyl vinyl ether | −50 | 400 | 66 | 28,100 | 2.07 |
| 18 | n-butyl vinyl ether | −78 | 400 | 62 | 117,000 | 1.13 |
| 19 | styrene | 19.8 | 400 | 83 | 14,400 | 1.86 |
| 20 | styrene | 0 | 400 | 83 | 26,500 | 1.69 |
| 21 | styrene | −50 | 400 | 6 | 143,600 | 1.31 |
| 22 | styrene | −78 | 400 | n.d. | n.d. | n.d. |
| 24 | α-methyl styrene | −78 | 400 | 24 | 53,300 | 1.52 | n.d. = not determined

Initiator (VI):

Synthesis of Synthesis of H(OEt$_2$)$_2$[Nb(1,2-O$_2$C$_6$Cl$_4$)$_3$] (VI)

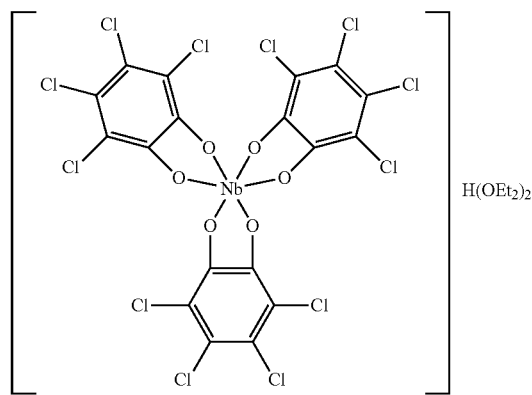

The synthesis of the initiator (Ill) described above may be adapted to replace the metal ion with niobium (Nb) to afford H(OEt$_2$)$_2$[Nb(1,2-O$_2$C$_6$Cl$_4$)$_3$] (VII).

Thus, NbCl$_5$ (0.25 g, 9.4 mmol) was stirred in anhydrous CH$_2$Cl$_2$ (8 mL) and the yellow suspension was slowly heated to reflux under N$_2$ atmosphere. In another Schlenk flask, tetrachlorocatechol (0.77 g, 31.1 mmol) was prepared in warm anhydrous CH$_2$Cl$_2$ (6 mL) and the bright orange-red solution was added via cannula to the refluxing NbCl$_5$ solution at 90° C. to afford a dark red reaction mixture. The reaction mixture was refluxed for 100 min and cooled to ambient temperature. Et$_2$O (20 mL) was added and the reaction mixture was stirred for 30 min. The solvent was removed under a reduced pressure at 0° C. The solid was collected by filtration, washed with CH$_2$Cl$_2$ (2 mL) and dried in vacuo. Yield=(0.42 g, 4.0 mmol, 42%).

$^1$H NMR (400 MHz, CD$_2$Cl$_2$, −80° C.): δ=16.73 (s, 1H, H(Et$_2$O)$_2$), 4.08 (br, 8H, OCH$_2$CH$_3$), 1.44 ppm (br, 12H, OCH$_2$CH$_3$) ppm.

Polymerization of Monomers Using Initiator (VI)

Polymerization of monomers with initiator (VI) was performed by following the general procedure described above for initiator (Ill). TABLE 5 shows data for the polymerization of n-butyl vinyl ether and styrene using initiator (VI). TABLE 5 shows that the niobium complex can also initiate cationic polymerization of n-butyl vinyl ether and styrene.

TABLE 5

| Ex. | Monomer | T (° C.) | [M]:[I] | Yield (%) | $M_n$ (g/mol) | PDI |
| --- | --- | --- | --- | --- | --- | --- |
| 25 | n-butyl vinyl ether | −78 | 400 | 76 | 32,800 | 1.39 |
| 26 | styrene | −78 | 400 | 71 | 10,400 | 4.41 |

Initiator (VII):

Synthesis of H[(OEt$_2$)]$_2$[Ta(1,2-O$_2$C$_6$H$_4$)$_3$]/ H(OEt$_2$)$_2$[Ta(1,2-O$_2$C$_6$H$_4$)$_2$(1,2-O$_2$C$_6$H$_5$)$_2$] (VII)

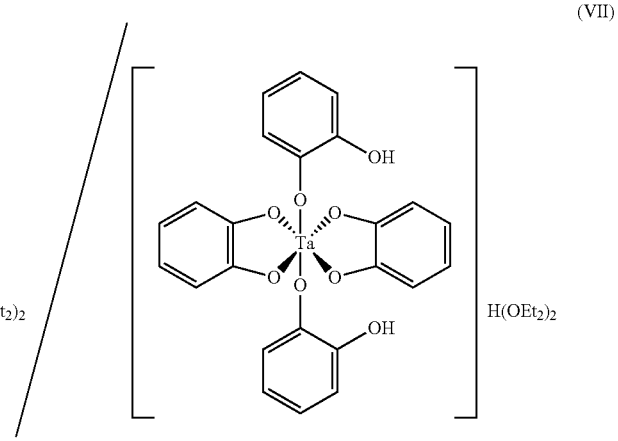

The reaction of 4 equivalents of catechol with TaCl$_5$ in a manner similar to the one described for the synthesis of the chlorinated analog (III) affords a mixture (VII) of the corresponding non-halogenated H[(OEt$_2$)]$_2$[Ta(1,2-O$_2$C$_6$H$_4$)$_3$] and a tantalum complex coordinated with four catechol ligands (two bidentate and two monodentate catechol ligands).

Thus, TaCl$_5$ (0.81 g, 22.7 mmol) was stirred in anhydrous CH$_2$Cl$_2$ (6 mL) and the white suspension was slowly heated to reflux under N$_2$ atmosphere. In another Schlenk flask, catechol (1.00 g, 90.8 mmol) was prepared in a solvent mixture containing anhydrous CH$_2$Cl$_2$ (6 mL) and anhydrous toluene (8 mL) and the bright orange-red solution mixture was warmed up to 50° C. and added via cannula to the refluxing TaCl$_5$ solution at 90° C. to afford a dark orange reaction mixture. After 10 min, a colorless precipitate was obtained. The reaction mixture was refluxed for 60 min and cooled to ambient temperature. The reaction mixture was stirred for another 120 min at ambient temperature. Upon addition of diethyl ether (18 mL), a yellow clear solution formed. The solution was cooled in an ice bath to afford a yellow precipitate within 30 min. The solid was collected by filtration, washed with CH$_2$Cl$_2$ (2 mL) and dried in vacuo. Yield=(0.58 g).

$^1$H NMR (400 MHz, CD$_2$Cl$_2$, 25° C.): δ=8.07-6.28 (m, Ar—H), 3.62 (br, 8H, OCH$_2$CH$_3$), 1.24 (t, $^3J_{HH}$=6.7H, OCH$_2$CH$_3$).

$^1$H NMR (400 MHz, CD$_2$Cl$_2$, −85° C.): δ=15.57 (s, 1H, H(OEt$_2$)$_2$), 10.28 (s, OH), 8.27-6.78 (m, Ar—H), 4.19 (br, 8H, OCH$_2$CH$_3$), 1.51 ppm (br, 12H, OCH$_2$CH$_3$) ppm.

Polymerization of Monomers Using a Mixture of Initiator (VII) with the Corresponding 4-Ligand Tantalum Complex Polymerization of monomers with initiator (VII) was performed by following the general procedure described above for initiator (III). TABLE 6 shows data for the polymerization of n-butyl vinyl ether, styrene and α-methyl styrene using initiator (VII) together with the corresponding 4-ligand tantalum complex. TABLE 6 shows that the balance of yield and molecular weight are generally poorer than for the chlorinated analog (III).

TABLE 6

| Ex. | Monomer | T (° C.) | [M]:[I] | Yield (%) | M$_n$ (g/mol) | PDI |
| --- | --- | --- | --- | --- | --- | --- |
| 27 | n-butyl vinyl ether | 19.6 | 400 | 29 | 14,500 | 1.48 |
| 28 | n-butyl vinyl ether | −78 | 400 | 17 | 96,400 | 1.33 |
| 29 | styrene | 19.6 | 400 | <1 | 43,300 | 1.28 |
| 30 | styrene | −50 | 400 | 1.2 | n.d. | n.d. |
| 31 | α-methyl styrene | 19.6 | 400 | <1 | 6,000 | 4.18 |
| 32 | α-methyl styrene | −50 | 400 | 1.7 | 10,900 | 1.60 |
| 33 | α-methyl styrene | −78 | 400 | 1.8 | 31,500 | 1.32 | n.d. = not determined

Use of Initiator (III) to Polymerize Isobutylene:

Isobutylene polymers (PIB) and isobutylene-isoprene copolymers (IIR-butyl rubber) were prepared using Initiator (III) by the following procedure.

Initiator (100 mg) was stirred in anhydrous CH$_2$Cl$_2$ (25 mL) for 30 minutes at −30° C. In another reaction flask, 6 mL of dry isobutylene (or 6 mL of dry isobutylene and 0.25 mL of isoprene when producing IIR) and 50 mL CH$_2$Cl$_2$ was stirred at −30° C., then 7 mL of the initiator solution was added. The reaction mixture was stirred for 17 minutes at −30° C. Afterwards, the polymerization was stopped by adding 0.1 mL alcohol containing 1 Molar tetrakis-[methylene-(3,5-di-tert-butyl-4-hydroxyhydrocinnamate)] methane (CAS #6683-19-8). The solvent was evaporated from the reaction mixture. The polymer residue was dissolved in hexane, filtered, and then the hexane removed to provide a polymer. TABLE 7 shows data for the preparation of PIB and IIR.

TABLE 7

| Ex. | Monomer | Initiator | Yield (%) | M$_n$ (g/mol) | PDI |
| --- | --- | --- | --- | --- | --- |
| 34 | isobutylene | (III) | 28 | 1,500 | 2.29 |
| 35 | isobutylene | (III) | 27 | 1,700 | 2.01 |
| 36 | isobutylene-isoprene | (III) | 45 | 2,000 | 2.35 |

With reference to FIG. 1, the $^1$H NMR spectrum of the polyisobutylene (PIB) produced in Ex. 34 is reactive PIB, having no terminal chloride. The PIB has a considerable proportion of terminal ethylenic unsaturation. The initiators therefore provide the opportunity to produce PIB and butyl polymers with reactive ends.

The novel features will become apparent to those of skill in the art upon examination of the description. It should be understood, however, that the scope of the claims should not be limited by the embodiments, but should be given the broadest interpretation consistent with the wording of the claims and the specification as a whole.

What is claimed is:

1. A Brønsted-Lowry acid initiator system for cationic polymerization of an ethylenically unsaturated monomer, the Brønsted-Lowry acid initiator system comprising an initiator having a structure of Formula (I) in an anhydrous polymerization medium:

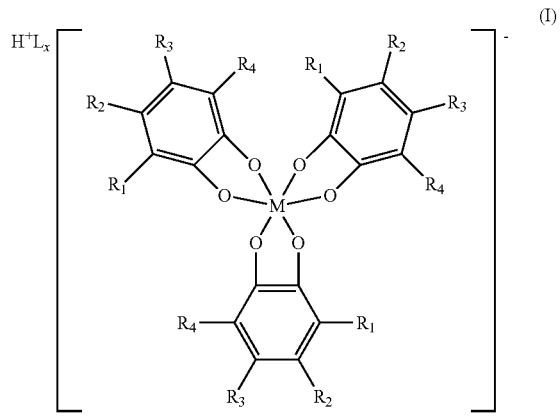

where:
  M is tantalum (Ta), vanadium (V) or niobium (Nb);
  R$_1$, R$_2$, R$_3$ and R$_4$ are the same or different and are independently H, F, Cl, Br, I, alkyl or aryl, or two or more of R$_2$, R$_3$, R$_4$ and R$_5$ on a same benzene ring are taken together to form a bicyclic, tricyclic or tetracyclic moiety with the benzene ring, with the proviso that all of R$_1$, R$_2$, R$_3$ and R$_4$ on the same benzene ring are not H;
  L is absent or a molecule that coordinates to H$^+$; and,
  x is 0 when L is absent, or x is 0.5 or more when L is present.

2. The system according to claim 1, wherein M is Ta.

3. The system according to claim 1, wherein L is a stabilizing molecule for the H$^+$ having one or more lone pairs of electrons.

4. The system according to claim 3, wherein L is a sterically-hindered molecule.

5. The system according to claim 1, wherein L is an alkyl ether or a cycloalkyl ether.

6. The system according to claim 1, wherein L is diethyl ether.

7. The system according to claim 1, wherein $R_1$, $R_2$, $R_3$ and $R_4$ are the same and are F or Cl.

8. The system according to claim 1, wherein: M is Ta; $R_1$, $R_2$, $R_3$ and $R_4$ are Cl; L is $Et_2O$; and, x is 2.

9. The system according to claim 1, wherein the anhydrous polymerization medium comprises dichloromethane or methyl chloride.

10. The system according to claim 1, containing substantially no water.

11. A process for producing a polymer, the process comprising polymerizing one or more ethylenically unsaturated monomers with the initiator system as defined in claim 1.

12. The process according to claim 11, wherein the polymerization is performed at a temperature of −85° C. or higher.

13. The process of claim 11, wherein M is Ta.

14. The process of claim 11, wherein L is a stabilizing molecule for the $H^+$ having one or more lone pairs of electrons.

15. The process of claim 14, wherein L is a sterically-hindered molecule.

16. The process of claim 11, wherein L is an alkyl ether or a cycloalkyl ether.

17. The process of claim 11, wherein
  i. L is diethyl ether; or
  ii. the anhydrous polymerization medium comprises dichloromethane or methyl chloride; or
  iii. the initiator system contains substantially no water.

18. The process of claim 11, wherein $R_1$, $R_2$, $R_3$ and $R_4$ are the same and are F or Cl.

19. The process of claim 11, wherein: M is Ta; $R_1$, $R_2$, $R_3$ and $R_4$ are Cl; L is $Et_2O$; and, x is 2.

* * * * *

UNITED STATES PATENT AND TRADEMARK OFFICE
CERTIFICATE OF CORRECTION

PATENT NO. : 11,168,100 B2
APPLICATION NO. : 16/771375
DATED : November 9, 2021
INVENTOR(S) : Arsenault et al.

Page 1 of 1

It is certified that error appears in the above-identified patent and that said Letters Patent is hereby corrected as shown below:

In the Claims

Column 15, Line 11 delete "and, x is 2." and insert --and x is 2.--

Column 16, Line 19 delete "and, x is 2." and insert --and x is 2.--

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*